(12) United States Patent
Iyengar et al.

(10) Patent No.: US 6,245,802 B1
(45) Date of Patent: *Jun. 12, 2001

(54) METHOD FOR TREATING PAIN

(75) Inventors: Smriti Iyengar, Carmel; Carrie Kimberly Jones, Indianapolis; Harlan Edgar Shannon, Carmel, all of IN (US)

(73) Assignee: Eli Lilly and Company, Indianapolis, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/438,191

(22) Filed: Nov. 11, 1999

Related U.S. Application Data

(60) Provisional application No. 60/108,370, filed on Nov. 13, 1998.

(51) Int. Cl.[7] .................................................. A61K 31/381
(52) U.S. Cl. ............................................ 514/438; 514/568
(58) Field of Search ...................................... 514/438, 568

(56) References Cited

FOREIGN PATENT DOCUMENTS

| 0 908 186 | 8/1998 | (EP) . |
|---|---|---|
| WO 97/35584 | 3/1997 | (WO) . |
| 98/46601 | * 10/1998 | (WO) . |

OTHER PUBLICATIONS

Mark J. Millan, et al., Way 100,635 enhances both the "antidepressant" actions of duloxetine and its influence on dialysate levels of serotonin in frontal cortex, *European Journal of Pharmacology* 341 (1998), pp. 165–167.

* cited by examiner

*Primary Examiner*—Phyllis G. Spivack
(74) *Attorney, Agent, or Firm*—Arvie J. Anderson; Suzanne M. Harvey

(57) ABSTRACT

The present invention provides a method for treating pain comprising administering to a mammal an analgesic composition comprising duloxetine and one or more NSAIDs or acetaminophen.

19 Claims, 2 Drawing Sheets

METHOD FOR TREATING PAIN

CROSS REFERENCE

This application claims priority of Provisional Application Ser. No. 60/108,370, filed Nov. 13, 1998.

BACKGROUND OF THE INVENTION

For many types of pain, the method for treating the pain is through administration of aspirin or any of a number of non-steroidal antiinflammatory agents, NSAIDs. Frequently, the administration of the NSAID provides the relief sought. However, if the relief of pain is insufficient with NSAIDs alone, these agents may be combined with orally effective morphine-like agents, such as codeine and other opioids. Because these two agents exert their effects by different mechanisms, combinations of these two classes of drugs usually can achieve an analgesic effect that would otherwise require a higher dose of opioid, but with fewer side effects. Nonetheless, even at a lesser dose of opioid, resulting in fewer side effects, it has been well documented that any dose of an opioid has the potential for severe side effects. For example, morphine and its related opioids may cause respiratory depression, nausea, vomiting, dizziness, mental clouding, dysphoria, pruritus, constipation, increased pressure in the biliary tract, urinary retention, hypotension, tolerance, and physical dependence. (*The Pharmacological Basis of Therapeutics*, 9th edition, Macmillan Publishing Co., 1996, pp 533–540.)

New safer and effective methods for the treatment of pain are in constant demand. The discovery of other agents which provide an analgesic synergism in combination with NSAIDs but have a reduction in the severity of the side effects profile are in constant demand. Such a combination is the subject of the present invention.

The present invention addresses a long felt need for a safe and effective treatment for pain.

SUMMARY OF THE INVENTION

The present invention provides a method for treating pain in a mammal requiring said treatment, which comprises administering to said mammal an effective amount of duloxetine or a pharmaceutically acceptable salt or solvate thereof; in combination with an effective amount of one or more NSAIDs.

The present invention also provides the use of duloxetine or a pharmaceutically acceptable salt or solvate thereof in combination with one or more NSAIDs for the manufacture of a medicament for treating pain.

Furthermore, the present invention provides the use of duloxetine or a pharmaceutically acceptable salt or solvate thereof in combination with one or more NSAIDs for treating persistent pain.

According to yet another aspect, the present invention provides a pharmaceutical formulation comprising a combination of duloxetine, or a pharmaceutically acceptable salt or solvate thereof, one or more NSAIDs, and a pharmaceutical carrier, diluent or excipient.

DETAILED DESCRIPTION OF THE INVENTION

Figure 1:
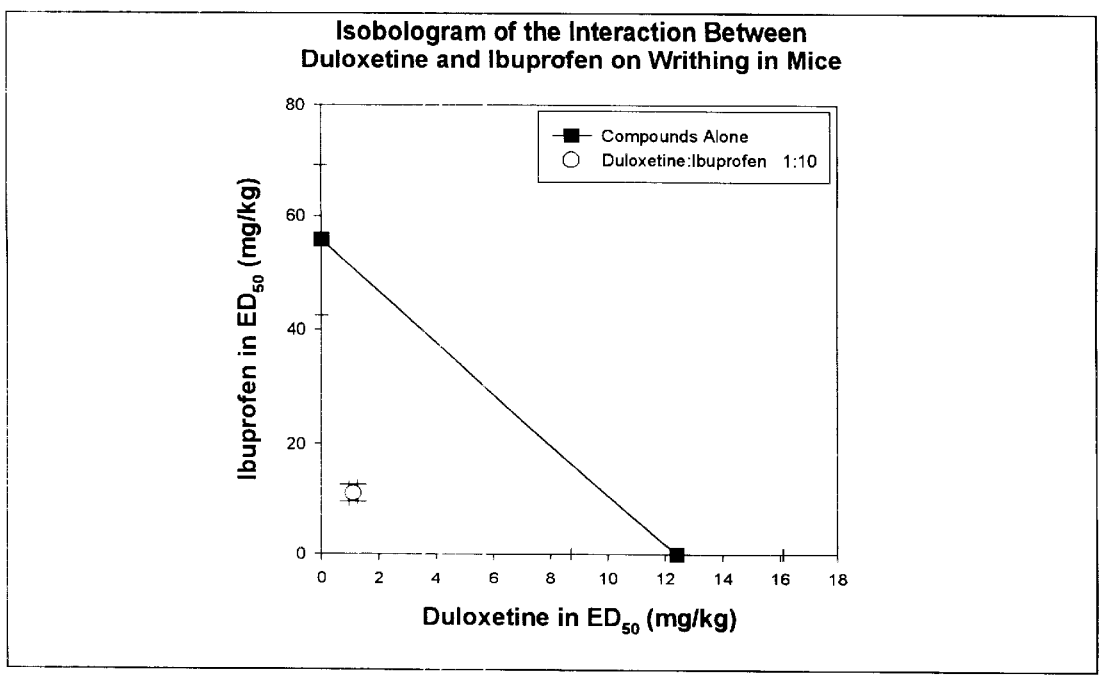
FIG. 1 is an Isobologram of the interaction between duloxetine and ibuprofen on writhing in mice.

The present invention provides a method for treating pain in a mammal requiring said treatment, which comprises administering to said mammal an effective amount of duloxetine or a pharmaceutically acceptable salt or solvate thereof; in combination with an effective amount of one or more NSAIDs.

Duloxetine, the (+)-enantiomer of N-methyl-3-(1-naphthalenyloxy)-3-(2-thienyl) propanamine, is usually administered as the hydrochloride salt. Duloxetine is represented in formula I:

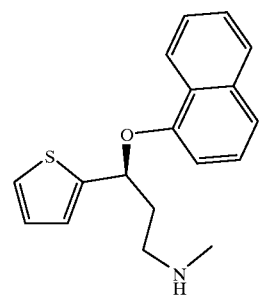

I

Duloxetine and its pharmaceutically acceptable salts and solvates were first taught by U.S. Pat. No. 4,956,388, the teachings of which are herein incorporated by reference in their entirety. The term "duloxetine" shall refer to any acid addition salt and the free base of the molecule.

In the method according to the invention, the term "combination" shall refer to the administration of duloxetine, or a pharmaceutically acceptable salt or solvate thereof; and one or more NSAIDs. The administration of the compounds may be in any order, or may be concurrent. For example, a mammal may be given the NSAIDs first, then given the duloxetine, or given the duloxetine first, then given the NSAIDs. Furthermore, the mammal may be given both, the duloxetine and the NSAIDs, concurrently.

In the method according to the invention, the term "treating" and "treatment" include prophylaxis or prevention of pain, amelioration or elimination of the developed pain once it has been established, or alleviation of the characteristic symptoms of such pain.

The skilled artisan will appreciate that pain is a heterogeneous disorder. In the method according to the invention, the term "pain" shall refer to all types of pain, including acute and persistent pain. Preferably, the term shall refer to persistent pains, such as, but not limited to, neuropathic pain, diabetic neuropathy, fibromyalgia, pain associated with somatoform disorders, arthritic pain, cancer pain, neck pain, shoulder pain, back pain, cluster headaches, tension-type headache, migraine, herpes neuralgia, phantom limb pain, central pain, dental pain, NSAID-resistant pain, visceral pain, surgical pain, post-operative pain, bone injury pain, pain during labor and delivery, pain resulting from burns, including sunburn, post-partum pain, angina pain, and genitourinary tract-related pain including cystitis. The term persistent pain shall also preferably refer to nociceptive pain or nociception.

The term "NSAID", as used herein, represents a nonsteroidal anti-inflammatory agent which can be identified as such by the skilled artisan. NSAIDs are known for their inhibition of cyclooxygenases I and II, the enzymes responsible for the biosynthesis of the prostaglandins and certain related autacoids. NSAIDs are known to be antipyretic, analgesic, and antiinflammatory. The term NSAID shall, in addition, refer to any compound acting as a non-steriodal antiinflammatory agent. For example, *The Pharmacological*

*Basis of Therapeutics*, 9th edition, Macmillan Publishing Co., 1996, pp 617–655, provides well known examples of NSAIDs. The term includes, but is not limited to, salicylic acid derivatives, such as salicylic acid, aspirin, methyl salicylate, diflunisal, salsalate, olsalazine, and sulfasalazine; para-aminophenol derivatives, such as acetaminophen; sulindac; etodolac; tolmetin; ketorolac; diclofenac; propionic acid derivatives, such as ibuprofen, naproxen, fenoprofen, ketoprofen, flurbiprofen, and oxaprozin; acetic acid derivatives, such as indomethacin; enolic acids, such as piroxicam; and cyclooxygenase II inhibitors, such as celecoxib, and rofecoxib. Applicants appreciate that new NSAIDs may be in development, and the present invention contemplates a synergistic combination and compositions comprising such new agents with duloxetine as well.

Preferably, the NSAID is selected from aspirin, ibuprofen, naproxen, celecoxib and rofecoxib.

Ibuprofen, celecoxib, and rofecoxib are particularly preferred NSAIDs in the method according to the invention.

According to a preferred aspect, the present invention provides a method for the treatment of pain in a mammal requiring said treatment, which comprises administering to said mammal an effective amount of ibuprofen, celecoxib, or rofecoxib and an effective amount of duloxetine or a pharmaceutically acceptable salt or solvate thereof.

According to a more preferred aspect, the present invention provides a method for the treatment of persistent pain in a mammal requiring said treatment, which comprises administering to said mammal an effective amount of ibuprofen, celecoxib, or rofecoxib and an effective amount of duloxetine or a pharmaceutically acceptable salt or solvate thereof.

In the methods according to the invention the mammal may be any animal in the Mammalian Class of higher vertebrates, for example a rodent, dog, cat, primate or human. Preferably the mammal is a human.

The effective amounts or dosages of NSAIDs and duloxetine administered will, of course, vary depending on known factors such as the pharmacodynamic characteristics of the particular agent, and its mode and route of administration; age, health, and weight of the recipient; nature and extent of the symptoms, kind of concurrent treatment, frequency of treatment, and the effect desired. Duloxetine is effective over a wide dosage range; however, it is desirable to administer a dosage that is as low as possible. Usually, the daily dosage can be such that the active ingredient is administered at a daily dosage of from about 0.2 mg to about 200 mg duloxetine and from about 0.6 to about 200 mg/kg of NSAIDs.

The amount of NSAIDs present in combination with duloxetine is adjusted in ratio to the duloxetine dosage. However, it will be understood that the amount of the compound actually administered will be determined by a physician in light of the relevant circumstances including the condition to be treated, the choice of compound to be administered, the age, weight, and response symptoms, and the chosen route of administration. Therefore the dosage ranges are not intended as a limitation to the scope of the invention.

The combination of duloxetine, or a pharmaceutically acceptable salt or solvate thereof, and one or more NSAIDs may be administered in a weight ratio of duloxetine to NSAIDs of from about 1 to about 100. As stated, the NSAIDs may be administered first, and then the duloxetine; duloxetine may be administered first, and then the NSAIDs; or they may both be administered concurrently.

A preferred combination is a weight ratio of duloxetine to NSAIDs of from about 1 to about 30. A further preferred ratio is from about 1 to about 10. A final preferred ratio is from about 1 to about 3.

While duloxetine and NSAIDs are preferably administered orally to mammals susceptible to or suffering from pain, they may also be administered by a variety of other routes such as the transdermal, parenteral, epidural, subcutaneous, intranasal, intramuscular and intravenous routes. Such formulations may be designed to provide delayed or controlled release using formulation techniques which are known in the art. It will substantially always be preferred, however, to administer both duloxetine and the NSAIDs as tablets or capsules and such pharmaceutical forms are recommended.

The materials for the present invention can be purchased or prepared by a variety of procedures well known to those of ordinary skill in the art. Duloxetine can be prepared as described by U.S. Pat. No. 4,956,388, previously incorporated by reference.

A preferred duloxetine enteric formulation is a pellet formulation comprising a) a core consisting of duloxetine and a pharmaceutically acceptable excipient; b) an optional separating layer; c) an enteric layer comprising hydroxypropylmethylcellulose acetate succinate (HPMCAS) and a pharmaceutically acceptable excipient; d) an optional finishing layer; as is described in U.S. Pat. No. 5,508,276, the teachings of which are herein incorporated by reference. The following formulation example demonstrates the preparation of such a preferred formulation.

FORMULATION EXAMPLE 10 mg Duloxetine Base/capsule

| Bill of Materials | |
| --- | --- |
| Beads | |
| Sucrose - starch nonpareils, 20–25 mesh | 60.28 mg |
| Duloxetine layer | |
| Duloxetine | 11.21 |
| Hydroxypropylmethylcellulose | 3.74 |
| Separating layer | |
| Hydroxypropylmethylcellulose | 2.51 |
| Sucrose | 5.00 |
| Talc, 500 mesh | 10.03 |
| Enteric layer | |
| HPMCAS, LF grade, Shin-Etsu Chemical Co., Tokyo Japan | 25.05 |
| Triethyl citrate | 5.00 |
| Talc, 500 mesh | 7.52 |
| Finishing layer | |
| Hydroxypropylmethylcellulose | 8.44 |
| Titanium dioxide | 2.81 |
| Talc | Trace |
| | 141.60 mg |

The duloxetine layer was built up by suspending duloxetine in a 4% w/w solution of the Hydroxypropylmethylcellulose in water, and milling the suspension with a CoBall Mill (Fryma Mashinen AG, Rheinfelden, Switzerland) model MS-12. A fluid bed dryer with a Wurster column was used to make this product, at a batch size of 1.0 kg. The separating layer was added from a 4% w/w solution of the Hydroxypropylmethylcellulose in water, in which the sucrose was also dissolved.

In order to prepare the enteric coating suspension, purified water was cooled to 10° C. and the polysorbate, triethyl citrate and silicone emulsion were added and dispersed or dissolved. Then the HPMCAS and talc were added and agitated until homogeneity was obtained, and the HPMCAS was fully neutralized by addition of ammonium hydroxide until solution of the polymer was complete. To this suspension, a carboxymethylcellulose aqueous solution, 0.5% w/w, was added and blended thoroughly. The enteric suspension was maintained at 20° C. during the coating process. The enteric suspension was then added to the partially completed pellets in the Wurster column at a spray rate of about 15 mL/min, holding the temperature of the inlet air at about 50° C. The product was dried in the Wurster at 50° C. when the enteric suspension had been fully added, and then dried on trays for 3 hours in a dry house at 60° C. A finishing layer was then applied which consisted of a 4.5% w/w Hydroxypropylmethylcellulose solution containing titanium dioxide and propylene glycol as plasticizer. The pellets were completely dried in the fluid bed dryer and then were filled in size 3 gelatin capsules.

Compositions suitable for internal administration contain from about one half (0.5) milligrams to about 600 milligrams of duloxetine or NSAID per unit. In these pharmaceutical compositions, duloxetine or NSAID will ordinarily be present in an amount of from about 0.5% to about 95% by weight based on the total weight of the composition.

Typical compositions include duloxetine or a pharmaceutically acceptable salt or solvate thereof and one or more NSAIDs, associated with a pharmaceutically acceptable excipient which may be a carrier, or a diluent or be diluted by a carrier, or enclosed within a carrier which can be in the form of a capsule, sachet, paper, or other container. In making the compositions, conventional techniques for the preparation of pharmaceutical compositions may be used. For example, the active compound will usually be mixed with a carrier which may be in the form of an ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone. The formulations may also include wetting agents, emulsifying and suspending agents, preserving agents, sweetening agents, or flavoring agents. The formulations of the invention may be formulated so as to provide quick, sustained, or delayed release of the active ingredient after administration to the patient by employing procedures well known in the art. The skilled artisan will appreciate that the compositions of duloxetine or one or more NSAIDs, as described prior, may also contain both duloxetine and one or more NSAIDs, in the same ratios as described for separate compositions.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parental application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

Generally, duloxetine is dispensed in unit form comprising from about 1 mg to about 200 mg in a pharmaceutically acceptable carrier per unit dosage.

Most preferably, the solid oral formulation of duloxetine or of duloxetine and one or more NSAIDs is contained in packaging materials which protect the formulation from moisture and light. For example, suitable packaging materials include amber colored high density polyethylene bottles, amber colored glass bottles, and other containers made of a material which inhibits the passage of light. Most preferably, the packaging will include a desiccant pack. The container may be sealed with an aluminum foil blister to provide the desired protection and maintain product stability. The following typical formulae are provided for the interest and information of the pharmaceutical scientist.

Formulation 1

Hard gelatin capsules are prepared using the following ingredients:

| | Quantity (mg/capsule) |
|---|---|
| (+)-Duloxetine, hydrochloride | 20 mg |
| Ibuprofen | 20 |
| Starch, dried | 150 |
| Magnesium stearate | 10 |
| Total | 200 mg |

Formulation 2

A tablet is prepared using the ingredients below:

| | Quantity (mg/capsule) |
|---|---|
| (+)-Duloxetine, hydrochloride | 10 |
| Ibuprofen | 10 |
| Cellulose, microcrystalline | 275 |
| Silicon dioxide, fumed | 10 |
| Stearic acid | 5 |
| Total | 310 mg |

The components are blended and compressed to form tablets each weighing 310 mg.

Formulation 3

An aerosol solution is prepared containing the following components:

| | Weight |
|---|---|
| Ibuprofen | 10 mg |
| (+)-Duloxetine, hydrochloride | 5 |

-continued

| | Weight |
|---|---|
| Ethanol | 25.75 |
| Propellant 22 (Chlorodifluoromethane) | 60.00 |
| Total | 100.75 mg |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 80 mg of active ingredient, are made as follows:

| | |
|---|---|
| Ibuprofen | 60 mg |
| (+)-Duloxetine, hydrochloride | 20 mg |
| Starch | 30 mg |
| Microcrystalline cellulose | 20 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 140 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 170 mg.

The following Examples are provided to better elucidate the practice of the present invention and should not be interpreted in any way as to limit the scope of the same.

Utility Test Methods

The unexpectedly enhanced analgesic activity of the composition of the invention was evidenced by tests initially conducted on mice. Mice weighing from about 18–30 grams at the time of testing were used for the following study. All mice were dosed by the oral route with vehicle, a dose of duloxetine, a dose of an NSAID, or a dose consisting of the combination of duloxetine and an NSAID. A stock suspension of NSAID was prepared in 5% acacia. All dosing suspensions were prepared by dilution of the stock suspension with distilled water.

Mouse Writhing Test

An accepted procedure for detecting and comparing the analgesic activity of different classes of analgesic drugs for which there is a good correlation with human analgesic activity is the prevention of acetic acid-induced writhing in mice. Mice are orally administered various doses of duloxetine in combination with ibuprofen, duloxetine alone, ibuprofen alone, and placebo prior to testing. The mice are then injected intraperitoneally with acetic acid (0.55% solution, 10 mL/kg) five minutes prior to a designated observation period. For scoring purposes "writhe" is indicated by whole body stretching or contracting of the abdomen during an observation period beginning about five minutes after receiving the acetic acid. Inhibition of writhing behavior is demonstrative of analgesic activity. Haubrich et al., "Pharmacology of pravadoline: a new analgesic agent", *The Journal of Pharmacology and Experimental Therapeutics*, 255 (1990) 511–522.

Doses of duloxetine in combination with ibuprofen were administered in a fixed-dose ratio of 1 part duloxetine and 10 parts ibuprofen. Duloxetine alone was dosed at 1.0, 3.0, 10 and 30 mg/kg. Ibuprofen alone was dosed at 10, 30, 100 and 300 mg/kg. Actual total doses of the combination of duloxetine and ibuprofen were 3, 10, 30 and 100 mg/kg.

All ED50 values and their standard error of means (SEM) were determined using accepted numerical methods. For example, see R. E. Kirk (1982) "Experimental Design: Procedures for the behavioral sciences," 2nd ed. The interaction of the dosages on acetic acid-induced writhing in mice is demonstrated by the Loewe isobologram (S. Loewe, *Pharm. Rev.* 9, 237–242 (1957).

The synergistic activity of a ratio of 1:10 duloxetine to ibuprofen on acetic acid-induced writhing in mice is demonstrated by the data in the Loewe isobologram in FIG. 1. In the isobolographic figure, the analgesic effects of duloxetine, referred to as the ED50 dosages, are presented on the X-axis and of ibuprofen on the Y-axis. The solid line connecting the ED50 dosages of duloxetine (alone) and NSAID (alone) represents the "ED50 addition line" which indicates the expected location of the ED50's for duloxetine and NSAID combinations if simple additivity were to describe their combined effects.

According to Loewe's isobolic theory, if the analgesic effects are simply additive to one another, then the expected location of the ED50's of duloxetine and NSAID component of each fixed dosage ratio would lie on the ED50 addition line. Combination ED50 values located significantly below the ED50 addition line would represent an unexpected synergistic effect of concomitant administration of duloxetine and ibuprofen and combination ED50 values located above the line would represent unexpected diminished analgesic effect. The open symbol represents the effects of duloxetine and ibuprofen administered in a fixed-dose ratio of 1 part duloxetine and 10 parts ibuprofen.

One method to establish the significance of such unexpected enhanced or diminished activity is to calculate the SEM values for each ED50. If the SEM values do not overlap the line of addition, then the ED50 values are significantly different from the line of addition.

The data presented in FIG. 1 show that administration of both duloxetine and ibuprofen show a statistically significant synergistic effect, since the dose combination ED50 value falls below the line of addition and neither the vertical nor horizontal SEMs overlap the line of addition.

Carrageenan-induced Thermal Hyperalgesia in Rats

Another accepted method for detecting and comparing the analgesic activity of different classes of analgesic compounds for which there is good correlation with human analgesic activity is the reversal of carrageenan-induced thermal hyperalgesia in rats (Hargreaves et al. *Pain* 32:77–88, 1988).

Rats were administered a dose of duloxetine, ibuprofen, duloxetine:ibuprofen in combination, or vehicle and then injected subcutaneously into one hindpaw with carrageenan (1.5% w/v, 100 μl). The response to a noxious thermal stimulus was determined two hours later using a commercially available thermal plantar device (Ugo Basil, Italy) according to established methods (Hargreaves et al. *Pain* 32:77–88, 1988). Briefly, animals were habituated to a plastic behavioral enclosure for 5 min. A heat source was positioned directly beneath a hindpaw and the time taken for hindpaw withdrawal monitored automatically. If the animal did not respond within 20 sec, the stimulus was automatically terminated to prevent tissue damage. Measurements for both the injured and contralateral (control) hindpaw were recorded. Thermal hyperalgesia is evidenced by a shorter response latency by the injured as compared to the control paw.

Duloxetine alone was administered at doses of 1.0, 3.0, 10 and 30 mg/kg. Ibuprofen alone was administered at doses of 10, 30, 100 and 300 mg/kg. Doses of duloxetine in combination with ibuprofen were administered in a fixed-dose ratio of 1 part duloxetine and 10 parts ibuprofen. Actual total doses of the combination were 1, 3, 10, 30, and 100 mg/kg.

All ED50 values and their standard error of means (SEM) were determined using accepted numerical methods. For example, see R. E. Kirk (1982) "Experimental Design: Procedures for the behavioral sciences," 2nd ed. The interaction of the dosages on carrageenan-induced thermal hyperalgesia in rats is demonstrated by the Loewe isobologram (S. Loewe, *Pharm. Rev.* 9, 237–242 (1957).

Figure 2:
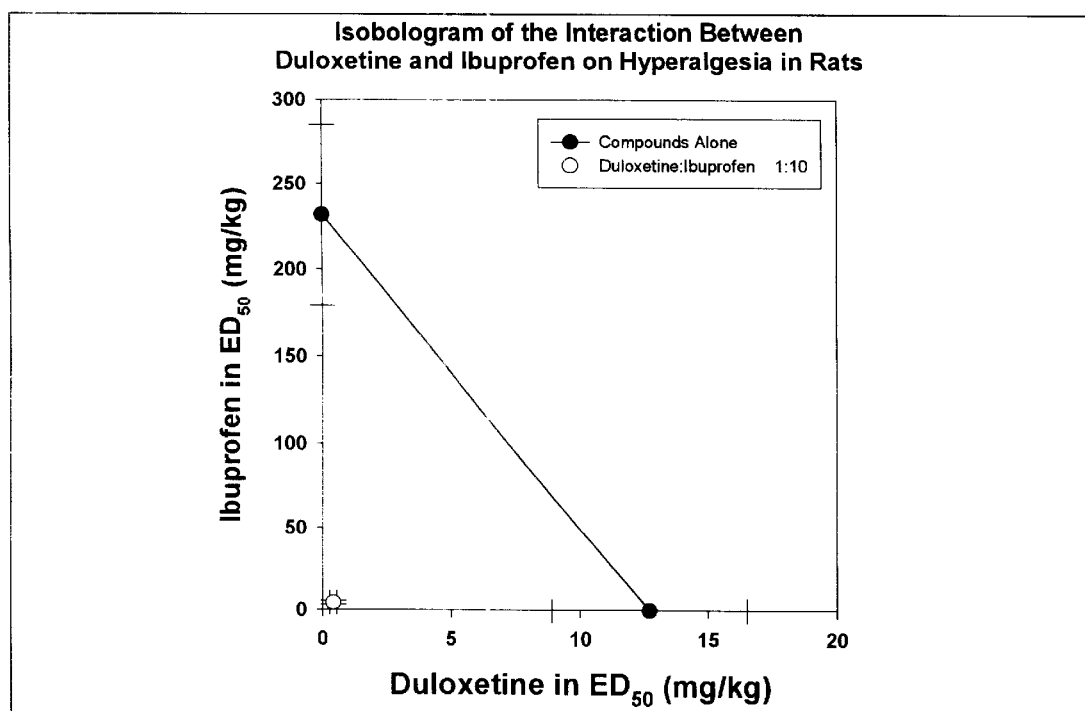
FIG. 2 is an Isobologram of the interaction between duloxetine and ibuprofen on hyperalgesia in rats.

The interaction of duloxetine and ibuprofen on carrageenan-induced thermal hyperalgesia in rats is demonstrated by the data in the Loewe isobologram in FIG. 2. In the isobolographic figure, the analgesic effects of duloxetine, referred to as ED50 dosages, are presented on the X-axis and of ibuprofen on the Y-axis. As above, the line connecting the ED50 dosages of duloxetine alone and ibuprofen alone represents the "ED50 addition line" which indicates the expected location of the ED50 values for duloxetine and ibuprofen combinations if simple additivity were to describe their combined effects. Combination ED50 values located significantly below the ED50 addition line would represent an unexpected synergistic effect of concomitant administration of duloxetine and ibuprofen and combination ED50 values located above the line would represent unexpected diminished analgesic effect. The open symbol represents the effects of duloxetine and ibuprofen administered in a fixed-dose ratio of 1 part duloxetine and 10 parts ibuprofen.

Data presented in FIG. 2 show that administration of both duloxetine and ibuprofen show a statistically significant synergistic effect, since the dose combination ED50 value falls below the line of addition and neither the vertical nor horizontal SEMs overlap the line of addition.

We claim:

1. A method for treating pain in a mammal requiring said treatment, which comprises administering to said mammal an effective amount of duloxetine or a pharmaceutically acceptable salt or solvate thereof; in combination with an effective amount of one or more NSAIDs or acetaminophen.

2. The method of claim 1 wherein the NSAID is selected from the group consisting of salicylic acid, aspirin, methyl salicylate, diflunisal, salsalate, olsalazine, sulfasalazine, indomethacin, sulindac, etodolac, tolmetin, ketorolac, diclofenac, ibuprofen, naproxen, fenoprofen, ketoprofen, flurbiprofen, oxaprozin, piroxicam, celecoxib, and rofecoxib.

3. The method of claim 2 wherein the NSAID is selected from the group consisting of aspirin, ibuprofen, naproxen, celecoxib, and rofecoxib.

4. The method of claim 3 wherein the NSAID is ibuprofen.

5. The method of claim 3 wherein the NSAID is celecoxib.

6. The method of claim 3 wherein the NSAID is rofecoxib.

7. The method of claim 1 wherein the pain is persistent pain.

8. The method of claim 7 wherein the persistent pain is selected from the group consisting of neuropathic pain, diabetic neuropathy, fibromyalgia, pain associated with somatoform disorders, arthritic pain, cancer pain, neck pain, shoulder pain, back pain, cluster headaches, tension-type headache, migraine, herpes neuralgia, phantom limb pain, central pain, dental pain, NSAID-resistant pain, visceral pain, surgical pain, post-operative pain, bone injury pain, pain during labor and delivery, pain resulting from burns, post-partum pain, angina pain, genitourinary tract-related pain, and nociceptive pain.

9. The method of claim 1 wherein the effective amount of duloxetine and the NSAID is in a weight ratio of from about 1 to about 10.

10. The method of claim 9 wherein the effective amount of duloxetine and the NSAID is in the weight ratio of from about 1 to about 3.

11. The method of claim 1 wherein the mammal is human.

12. The method of claim 1 wherein duloxetine is the hydrochloride salt.

13. A pharmaceutical formulation consisting essentially of duloxetine, or a pharmaceutically acceptable salt or solvate thereof, one or more NSAIDs or acetaminophen, and a pharmaceutical carrier, diluent, or excipient.

14. The formulation of claim 13 wherein the NSAID is selected from the group consisting of salicylic acid, aspirin, methyl salicylate, diflunisal, salsalate, olsalazine, sulfasalazine, indomethacin, sulindac, etodolac, tolmetin, ketorolac, diclofenac, ibuprofen, naproxen, fenoprofen, ketoprofen, flurbiprofen, oxaprozin, piroxicam, celecoxib, and rofecoxib.

15. The formulation of claim 14 wherein the NSAID is selected from the group consisting of aspirin, ibuprofen, naproxen, celecoxib and rofecoxib.

16. The formulation of claim 15 wherein the NSAID is ibuprofen.

17. The formulation of claim 15 wherein the NSAID is celecoxib.

18. The formulation of claim 15 wherein the NSAID is rofecoxib.

19. The formulation of claim 13 wherein duloxetine is the hydrochloride salt.

* * * * *